(12) United States Patent
Bratkovski et al.

(10) Patent No.: US 7,995,201 B2
(45) Date of Patent: Aug. 9, 2011

(54) PLASMONIC ELECTRIC-FIELD CONCENTRATOR ARRAYS AND SYSTEMS FOR PERFORMING RAMAN SPECTROSCOPY

(75) Inventors: Alexandre M. Bratkovski, Mountain View, CA (US); Ekaterina Viktorovna Ponizovskaya, Sunnyvale, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 253 days.

(21) Appl. No.: 12/287,549

(22) Filed: Oct. 10, 2008

(65) Prior Publication Data

US 2010/0091274 A1    Apr. 15, 2010

(51) Int. Cl.
*G01J 3/44* (2006.01)
(52) U.S. Cl. .................................................... 356/301
(58) Field of Classification Search .................... 356/301
See application file for complete search history.

(56) References Cited

U.S. PATENT DOCUMENTS

| 5,255,067 A * | 10/1993 | Carrabba et al. ............... 356/301 |
| 7,733,481 B1 * | 6/2010 | Bratkovski et al. ........... 356/301 |
| 2003/0059820 A1 * | 3/2003 | Vo-Dinh ........................ 356/301 |
| 2003/0231304 A1 * | 12/2003 | Chan et al. ..................... 356/301 |
| 2006/0055922 A1 * | 3/2006 | Li et al. ......................... 356/301 |
| 2006/0119853 A1 * | 6/2006 | Baumberg et al. ............. 356/301 |
| 2006/0183236 A1 * | 8/2006 | Berlin et al. .................... 436/94 |
| 2007/0252982 A1 * | 11/2007 | Wang et al. .................... 356/301 |

* cited by examiner

*Primary Examiner* — Kars E Geisel

(57) ABSTRACT

Various embodiments of the present invention relate to plasmonic electric-field concentrators and to systems incorporating the plasmonic electric-field concentrators to perform Raman spectroscopy. In one aspect, a plasmonic electric-field concentrator comprises two or more large features, and a relatively small feature similar in shape to large features positioned adjacent to the two or more large features. The features are arranged so that when light of an appropriate wavelength is incident on the features, surface plasmon polaritons form on the outer surfaces of the features. The surface plasmon polaritons have associated electric fields extending perpendicular to the surfaces of the features. The electric fields are concentrated in the space between features forming an electric field hot spot that enhances Raman scattered light emitted from an analyte proximate to or absorbed on the features.

20 Claims, 13 Drawing Sheets

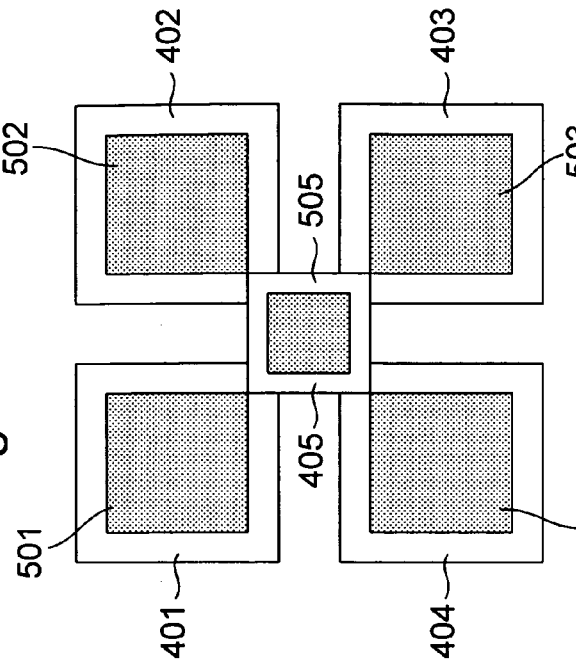
Figure 6A
Figure 6B
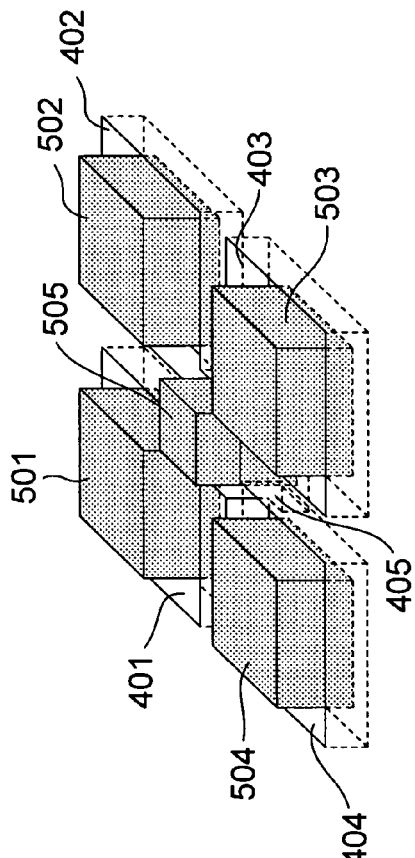
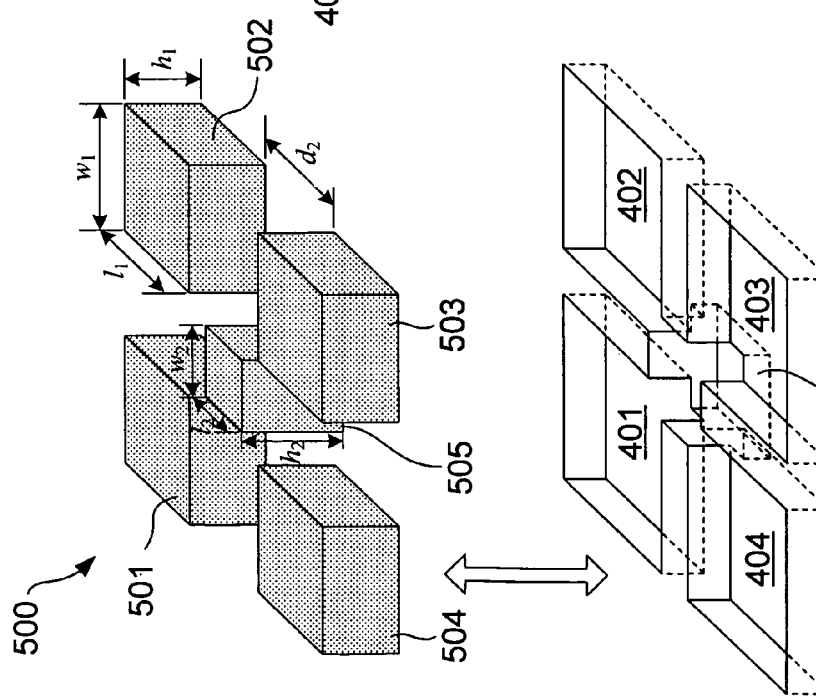
Figure 5

PLASMONIC ELECTRIC-FIELD CONCENTRATOR ARRAYS AND SYSTEMS FOR PERFORMING RAMAN SPECTROSCOPY

TECHNICAL FIELD

Embodiments of the present invention relate generally to systems for performing surface-enhanced Raman spectroscopy.

BACKGROUND

Raman spectroscopy is a spectroscopic technique used in condensed matter physics and chemistry to study vibrational, rotational, and other low-frequency modes in a molecular system. In a Raman spectroscopic experiment, a monochromatic beam of light, typically in the ultraviolet, visible, or infrared regions of the electromagnetic spectrum, passes through a sample of molecules and a spectrum of scattered light is emitted. The term "light" refers to electromagnetic radiation having wavelengths within the visible and non-visible portions of the electromagnetic spectrum, such as the ultraviolet and infrared portions of the spectrum. The spectrum of light emitted from the molecule is called a "Raman spectrum" and the scattered light is also called "Raman scattered light." A Raman spectrum can reveal electronic, vibrational, and rotational energies levels of a molecule. Different molecules produce different Raman spectrums that can be used like a fingerprint to identify molecules and even determine the structure of molecules. For example, Raman gas analyzers have many practical applications such as providing real-time monitoring of molecular changes in gas mixtures.

The Raman scattered light generated by a compound (or ion) adsorbed on or within a few nanometers of a structured metal surface can be $10^3$-$10^6$ times greater than the Raman scattered light generated by the same compound in solution. This surface-enhanced Raman scattering ("SERS") is strongest on silver ("Ag"), gold ("Au"), and copper ("Cu") surfaces. SERS arises from two mechanisms. The first mechanism is an enhanced electromagnetic field produced at the surface of a metal. When the wavelength of incident light is close to the plasma wavelength of the metal, conduction electrons in the metal surface are excited into an extended surface, excited electronic state called a "surface plasmon." Molecules adsorbed or in close proximity to the surface experience a relatively strong electromagnetic field. Molecular vibrational modes directed normal to the surface are most strongly enhanced. The intensity of the surface plasmon resonance is dependent on many factors including the wavelength of the incident light and the morphology of the metal surface. The second mode of enhancement occurs from the formation of a charge-transfer complex between the surface and a molecule absorbed to the surface. The electronic transitions of many charge transfer complexes are typically in the visible range of the electromagnetic spectrum.

In recent years, SERS has emerged as a routine and powerful tool for investigating molecular structures and characterizing interfacial and thin-film systems, and even enables single-molecule detection. In spite of its recent popularity, SERS does have limitations, including strict requirements that must be met in order to achieve optimal enhancement, which is usually extremely non-uniform over a SERS-active substrate. One critical aspect of SERS involves producing an ideal reproducible surface morphology for maximum field enhancement that is uniform over the active substrate. However, achieving an ideal reproducible surface morphology with homogeneous high performance (high and uniform enhancement factor) has been quite daunting and elusive. In addition, typical optical systems for performing Raman spectroscopy is very large and consists of an optical microscope that focuses light from a source onto an analyte and the Raman spectrum emitted from the analyte is gathered through the same optical system. Collecting an emission spectrum in this manner is inefficient and these optical systems are often bulky. Thus, engineers, physicists, and chemists continue to seek improvements in substrate surface morphology and improvements in systems for performing surface enhanced Raman spectroscopy.

SUMMARY

Various embodiments of the present invention relate to plasmonic electric-field concentrators and to systems incorporating the plasmonic electric-field concentrators to perform Raman spectroscopy. In one aspect, a plasmonic electric-field concentrator comprises two or more features having a first size, and a feature having a second size that is similar in shape and positioned adjacent to the two or more features. The features are arranged so that when light of an appropriate wavelength is incident on the features, surface plasmon polaritons form on the outer surfaces of the features. The surface plasmon polaritons have associated electric fields extending substantially perpendicular to the surfaces of the features. The electric fields are concentrated near the small feature forming an electric field hot spot around the smaller feature that enhances Raman scattered light emitted from a molecule proximate to or absorbed on the features.

BRIEF DESCRIPTION OF THE DRAWINGS

FIG. 5 shows an exploded isometric view of a plasmonic electric-field concentrator configured in accordance with embodiments of the present invention.

FIG. 6A shows an isometric view of cuboid-shaped features disposed in recesses of a substrate in accordance with embodiments of the present invention.

FIG. 6B shows a top plan view the cuboid-shaped features disposed in the recesses shown in FIG. 6A in accordance with embodiments of the present invention.

DETAILED DESCRIPTION

Embodiments of the present invention relate to plasmonic electric-field concentrators ("PEFCs") and to systems for performing surface enhanced Raman spectroscopy. Interaction substrates are formed from arrays of PEFCs, and the interaction substrates are incorporated into systems for performing surface enhance Raman spectroscopy. When incident light of an appropriate wavelength impinges on a PEFC, surface plasmon polaritons are formed on PEFC features. The features are configured and arranged to concentrate and enhance the intensity of the electric fields produced by the surface plasmon polaritons. The concentrated electric field in turn enhances the emission of Raman scattered light from analytes located in proximity to or absorbed on the interaction substrates. The systems for performing Raman spectroscopy incorporating the PEFC-based interaction substrates can be portable, energy efficient, and configured to exploit the coherency of the incident light.

Interaction Substrates and Plasmonic Electric-Field Concentrators

Figure 1A:
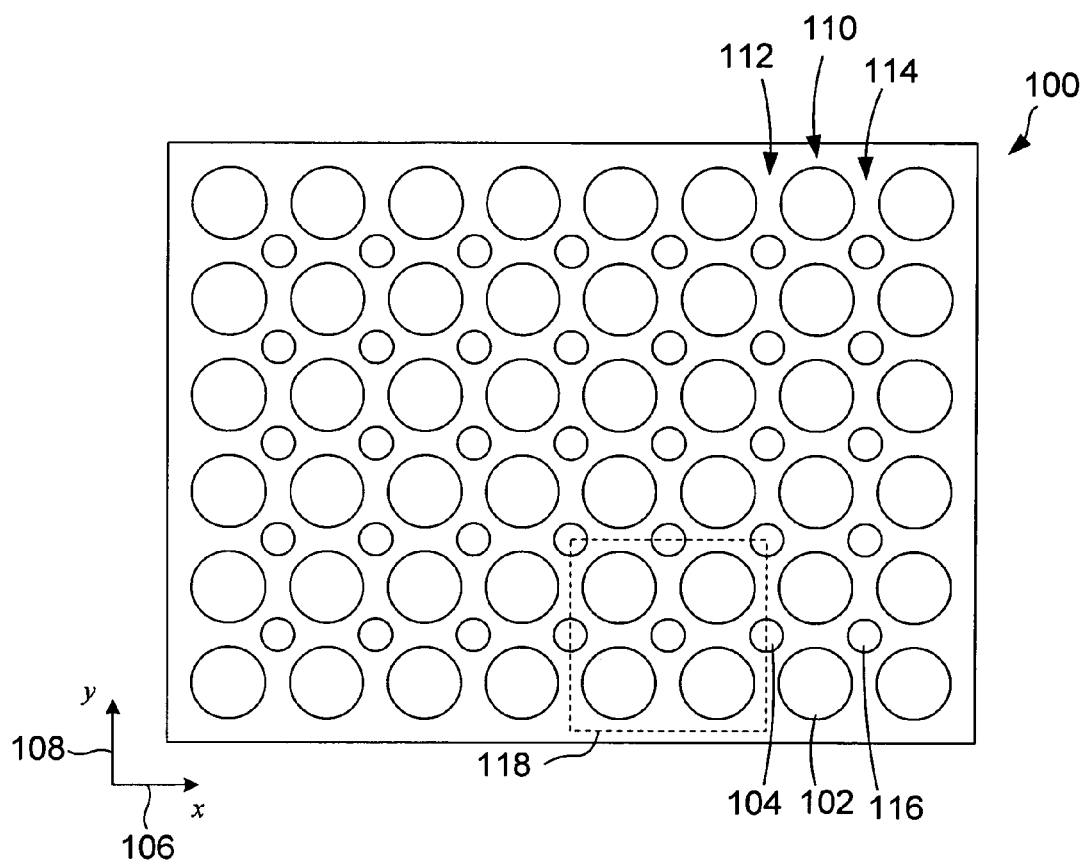
FIG. 1A shows a top plan view and general representation of an interaction substrate configured in accordance with embodiments of the present invention.

FIG. 1A shows a top plan view and general representation of an interaction substrate 100 configured in accordance with embodiments of the present invention. The substrate 100 includes a first array of circular-shaped features, such as feature 102, and a second array of relatively smaller circular-shaped features, such as feature 104. The features are not limited to circular shapes and, in other embodiments, the features can be square, rectangular, elliptical, star-shaped, irregular-shaped, or have any other suitable geometry. The features of the first and second arrays are regularly spaced, and the features within each array are arranged in rows and columns running substantially parallel to x-axis 106 and y-axis 108. FIG. 1A reveals that the features are interspersed so that each row or column of the relatively smaller features of the second array is a row or column of relatively larger features in the first array. For example, feature 102 lies within a column of substantially regularly spaced large features 110 that are disposed between columns of substantially regularly spaced relatively smaller features 112 and 114, such as features 104 and 116. The first and second arrays of features are also arranged so that each of the relatively smaller features of the second array are adjacent to and approximately the same distance from four relatively larger features of the first array that combined form an array of plasmonic electric-field concentrators ("PEFCs"). For example, dashed-line square 118 encompasses a PEFC comprising a relatively smaller feature of the second array adjacent to four relatively larger features of the first array.

Figure 1B:
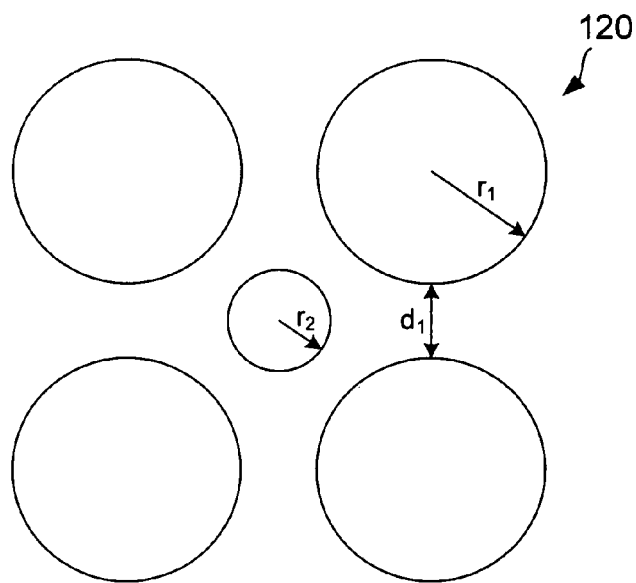
FIG. 1B shows an enlargement of a plasmonic electric field concentrator configured in accordance with embodiments of the present invention.

FIG. 1B shows an enlargement of a PEFC 120 configured in accordance with embodiments of the present invention. The parameters $r_1$ and $r_2$ represent the radii of the larger and relatively smaller features, respectively, where $r_1 > r_2$. The parameter $d_1$ represents the separation distance or gap between adjacent relatively larger features. The radii $r_1$ and $r_2$ and the separation distance $d_1$ are typically on the order of tens of nanometers. For example, the radius $r_1$ can range from about 30 to about 100 nm, the radius $r_2$ can range from about 10 nm to about 25 nm, and the separation distance $d_1$ can range from between about 1 to about 10 nm.

Figure 2A:
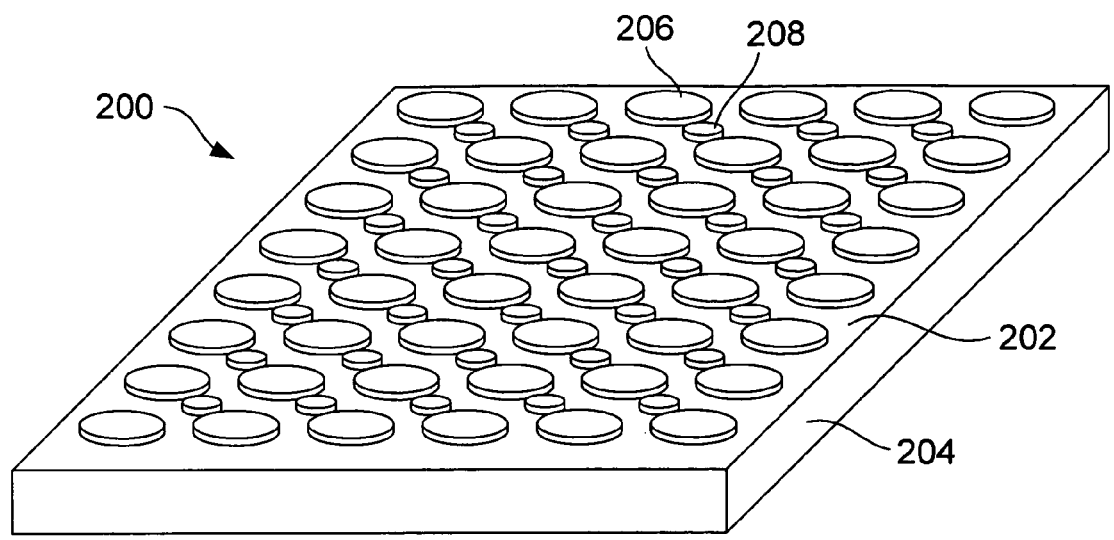
FIG. 2A shows an isometric view of a first interaction substrate configured in accordance with embodiments of the present invention.

In certain embodiments, the features comprising the interaction substrate 100 can be thin plates and disposed on a substrate. FIG. 2A shows an isometric view of a first interaction substrate 200 configured in accordance with embodiments of the present invention. The interaction substrate 200 comprises two interspersed arrays of disk-shaped, plate-like features disposed and arranged on a surface 202 of a substrate 204. The first array comprises large disk-shaped features, such as feature 206, and the second array comprises relatively smaller disk-shaped features, such as feature 208, interspersed within the features of the first array, as described above with reference to FIG. 1A. The disk-shaped features can be composed of Ag, Au, Cu, or another suitable material for supporting the formation of surface plasmon polaritons. The substrate 204 can be composed of $SiO_2$, glass, or another suitable dielectric material. The thickness of the disk-shaped features is on the order of tens of nanometers. In certain embodiments, the thickness can range from about 5 nm to about 20 nm.

The disk-shaped features can be formed by first depositing a relatively thin layer of metal on the surface 202 using sputtering, chemical vapor deposition, plasma enhanced chemical vapor deposition, physical vapor deposition, or an other suitable technique for depositing a metallic layer. The thin metallic layer can then be masked with a resist having the pattern of the first and second arrays of disk-shaped features, and the disk-shaped features formed by etching away the metal between the resists using reactive-ion etching, focused ion beam milling, or any other technique for removing portions of the layer of metal leaving a pattern of interspersed arrays of disk-shaped features.

Figure 2B:
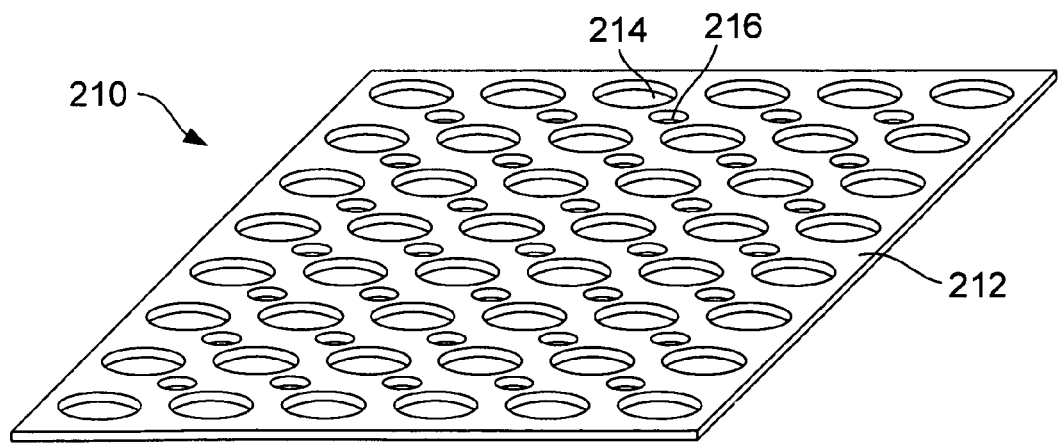
FIG. 2B shows an isometric view of a second interaction substrate configured in accordance with embodiments of the present invention.

In other embodiments, the features comprising the interaction substrate 100 can be holes formed in a metallic film. FIG. 2B shows an isometric view of a second interaction substrate 210 configured in accordance with embodiments of the present invention. The interaction substrate 210 comprises a thin metallic film 212 including two interspersed arrays of features. The first array of features comprises large circular-shaped holes, such as hole 214, and the second array comprises relatively smaller circular-shaped holes, such as hole 216, interspersed between the holes of the first array, as described above with reference to FIG. 1A. The thin metallic film 212 can be composed of Ag, Au, Cu, or another suitable material for supporting the formation of SPPs. The thickness of the film 212 is on the order of tens of nanometers. In certain embodiments, the thickness can range from about 5 nm to about 20 nm.

In certain embodiments, the interaction substrate 210 can be disposed on the surface of a dielectric substrate, such as SiO$_2$ or glass, and in other embodiments, the interaction substrate 210 can be a suspended platform supported around the edges by dielectric support structures or walls.

The interaction substrate 210 can be formed by masking a metallic film with a resist having a pattern of holes corresponding to the pattern of holes in the first and second arrays of holes. The holes can be formed using lithography followed by lift-off or by nanoimprint lithography followed by lift-off.

Figure 3A:
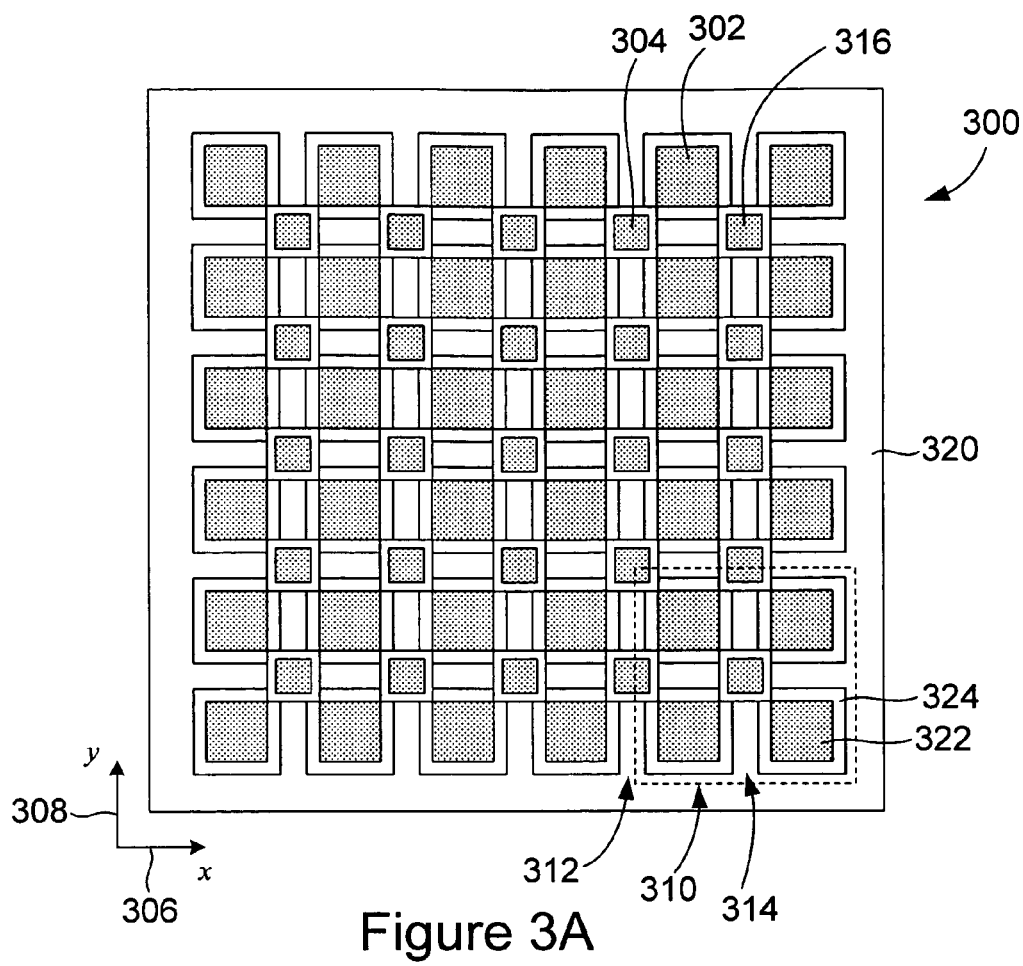
FIG. 3A shows a top plan view of a third interaction substrate configured in accordance with embodiments of the present invention.
Figure 3B:
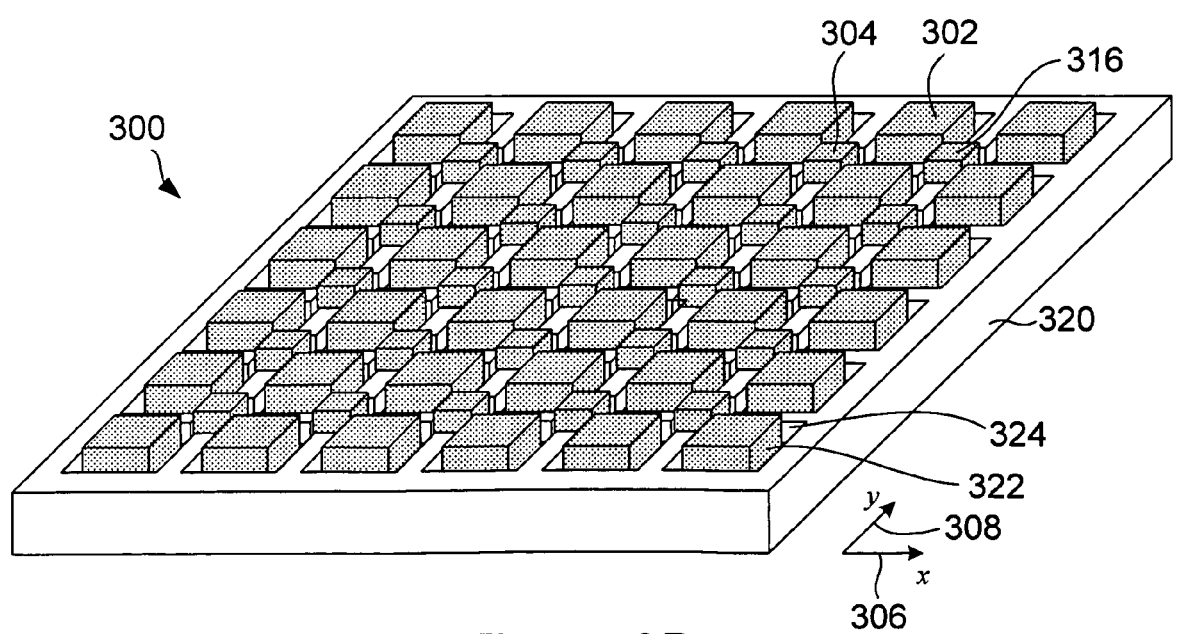
FIG. 3B shows an isometric view of the third interaction substrate configured in accordance with embodiments of the present invention.

In other embodiments, the features of the PEFCs can have polyhedral shapes. FIGS. 3A-3B show a top plan view and an isometric view, respectively, of a third interaction substrate 300 configured in accordance with embodiments of the present invention. The substrate 300 includes a first array of features, such as feature 302, and a second array of relatively smaller features, such as feature 304. The features of the first and second arrays are regularly-spaced regular parallelepipeds called "cuboids." The features of the second array are interspersed among the relatively larger features of the first array. Like the interaction substrate 100, the features within each array are arranged in rows and columns running parallel to x-axis 306 and y-axis 308. For example, feature 302 lies within a column of substantially regularly spaced features 310 that are disposed between columns of substantially regularly-spaced relatively-smaller features 312 and 314, such as features 304 and 316. FIG. 3A also reveals that the relatively smaller features of the second array are adjacent to and approximately the same distance from four relatively larger features of the first array forming an array of PEFCs, such as the PEFC encompassed by dashed-line square 318. FIGS. 3A-3B also reveal that each feature is disposed within a recess formed in a substrate 320. For example, feature 322 is disposed within a recess 324.

Figure 4A:
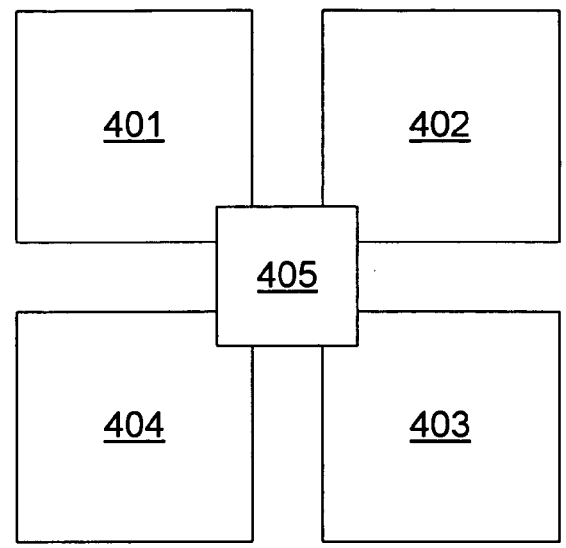
FIG. 4A shows a top plan view of five recesses formed in a substrate for supporting cuboid-shaped features of a plasmonic electric-field concentrator configured in accordance with embodiments of the present invention.
Figure 4B:
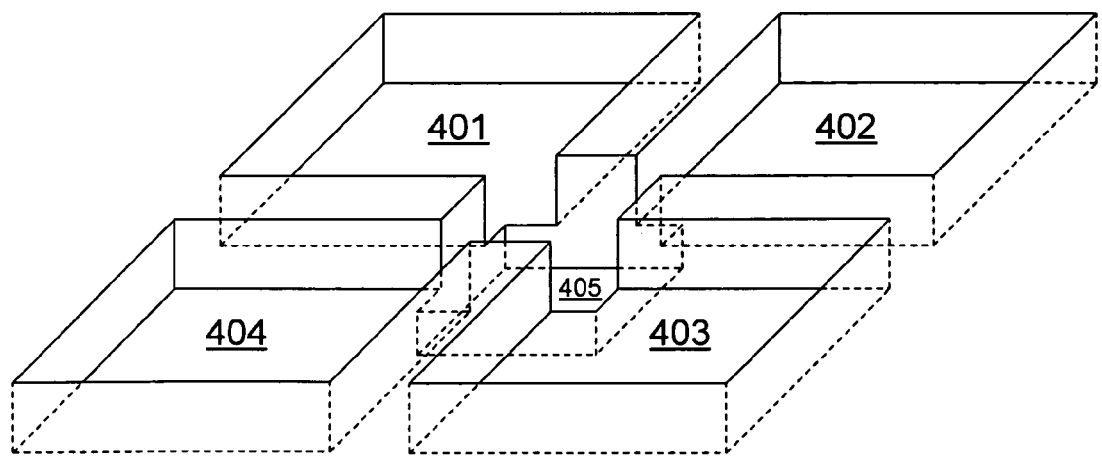
FIG. 4B shows an isometric view of five recesses formed in a substrate for supporting cuboid-shaped features of a plasmonic electric-field concentrator configured in accordance with embodiments of the present invention.

FIGS. 4A-4B show a top plan view and an isometric view of five recesses formed in a substrate for supporting polyhedral features of a PEFC configured in accordance with embodiments of the present invention. As shown in FIG. 4A, four of the five recesses 401-404 are arranged in a substantially square configuration with the fifth centrally located recess 405 overlapping portions of the four recesses 401-404. FIG. 4B reveals that the fifth recess 405 is deeper than the four recesses 401-404. In other embodiments, the recesses can be circular, elliptical, rectangular, irregular-shaped, or have any other suitable geometry.

FIG. 5 shows an exploded isometric view of a PEFC 500 configured in accordance with embodiments of the present invention. The PEFC 500 includes five cuboid-shaped features 501-505 separated from corresponding recesses 401-405. The lengths $l_1$ and $l_2$, widths $w_1$ and $w_2$, and heights $h_1$ and $h_2$ of the large cuboid-shaped features 501-504 are on the order of tens of nanometers, and the separation distance or gap $d_2$ between relatively larger sized cuboid-shaped features is also on the order of tens of nanometers. For example, large cubic features can have length, width, and height dimensions of about 90 nm, a relatively smaller cubic feature can have length, width, and height dimensions of about 30 nm, and the separation distance $d_2$ can range from about 1 to about 15 nm.

FIGS. 6A-6B show isometric and top plan views, respectively, of the cuboid-shaped features 501-504 disposed in the recesses 401-405 in accordance with embodiments of the present invention. The cuboid-shaped features can be composed of Ag, Au, Cu, or another suitable material for supporting the formation of surface plasmons, and the substrate in which the recesses 401-405 are formed can be composed of SiO$_2$, glass, or another suitable dielectric material.

Figure 7B:
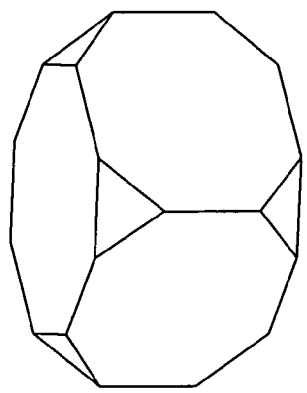
FIGS. 7A-7D show examples of four kinds of polyhedral shapes of features configured with in accordance with embodiments of the present invention.
Figure 7D:
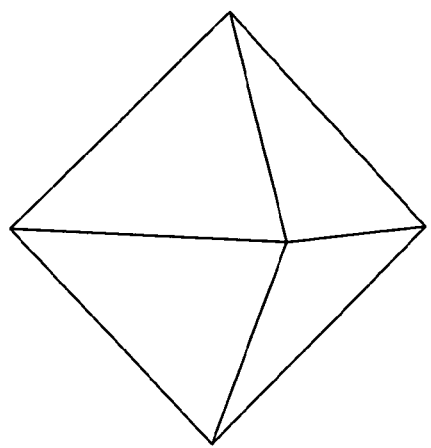
Figure 7A:
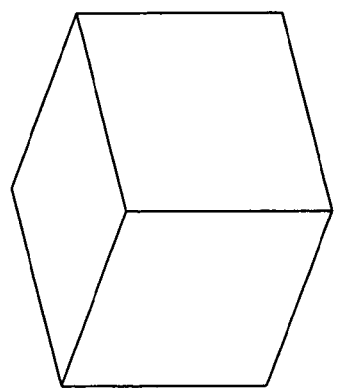
Figure 7C:
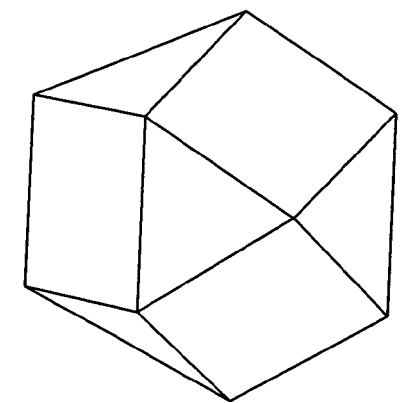

Embodiments of the present invention are not limited to cuboid-shaped features. FIGS. 7A-7D show examples of four kinds of polyhedral shapes the features can have in accordance with embodiments of the present invention. The features can be configured as a cube, as shown in FIG. 7A, a truncated cube, as shown in FIG. 7B, a cubohedron, as shown in FIG. 7C, and an octahedron, as shown in FIG. 7D. The features can also assume a tetrahedral, a regular or irregular star shape, or any other suitable polyhedral shape. The ultimate shape of the polyhedral features can depend on the crystal structure of the material comprising the features, the size of the features, and the conditions under which the features are formed.

Templated self-assembly can be used to fabricate an interaction substrate, such as the interaction substrate 300. Using nanoimprint lithography or another suitable lithographic technique, the interaction substrate can be configured by patterning the recesses described above with reference to FIG. 4 into a substrate slab composed of a dielectric material, such as a slab composed of SiO$_2$ or glass or silicon nitride. Once the substrate has been patterned with a periodic array of recesses, the larger features can be guided into the correspondingly larger recesses followed by depositing the relatively smaller features to fill the relatively smaller recesses between the larger features. The features can be formed in a separate assembly process using a Langmuir-Blodgett technique and transferred to the templated interaction substrate.

The interaction substrates 100 and 300 are not limited to having two arrays of interspersed features. In other embodiments, interaction substrates can be formed from three or more arrays of interspersed features. In addition, the geometry or polyhedral shape of the features comprising the arrays of relatively smaller features does not have to match the geometry or polyhedral shape of larger features in the array of relatively larger features. For example, in other embodiments, the second array of relatively smaller features of the interaction substrate 100 can have substantially square-shaped geometries, while the first array of relatively larger features can have circular geometries. In still other embodiments, the second array of relatively smaller features of the interaction substrate 300 can be non-cuboidal polyhedrons, such as octahedrons or truncated cubes, while the features of the first array can be relatively larger cuboids.

Operation of Plasmonic Electric-Field Concentrators

The arrangement of relatively smaller features disposed adjacent to relatively larger features of a PEFC enhances the formation of electric fields around the relatively smaller features of the PEFC. Light of an appropriate wavelength incident on the features of the PEFCs 200, 210, and 500 interacts with the electrons in the features to form electron-plasma oscillations along the outer surfaces of the features. These quantized electron-plasma oscillations are referred to as surface plasmon polaritons ("SPPs"), and the oscillations produce corresponding electron excitations that exist on the surface of the features. The SPPs have longitudinal and transverse electromagnetic field components. The magnetic field component is approximately parallel to the outer surface, while the electric field component is perpendicular to the outer surface and has a high intensity within a few tens of nanometers from the outer surface (transverse magnetic-waves).

The SPPs of the features comprising a PEFC all have substantially the same resonant frequency. In other words, the electric fields produced by the features with the same shape all oscillate with substantially the same resonant frequency.

The electric field associated with the relatively smaller feature oscillates in an already large oscillating electric field produced by the relatively larger features. The small electric field produced by the relatively smaller feature creates a perturbation that in combination with the electric fields produced by adjacent larger features amplifies the intensify the electric field around the features creating electric field "hot spot." Hot spots are the highest intensity portions of the electric field created by a PEFC. A hot spot occupies a region surrounding smaller plate-like or polyhedral-shaped features and can extend into the region between the smaller feature and the adjacent relatively larger features. A hot spot can also occupy regions within the smaller holes and can extend into portions of relatively larger adjacent holes.

The PEFCs intensify the Raman scattered light emitted from an analyte interacting with light of an appropriate wavelength and an interaction substrate. The wavelength of incident light is selected to interact with the analyte and the features of the PEFC to form SPPs on the features. The localized SPPs produce electric fields that are intensified at the hot spots of the PEFCs. In general, the electric field produced by the features is greatest when the SPP frequency is resonant with the wavelength of the incident light. In order for Raman scattering to occur, the electric fields at the features excite the Raman modes of the analyte molecules. However, PEFC embodiments of the present invention are configured to further enhance the intensity the electric fields at the hots the hot spots. As a result, the higher intensity electric fields at the hot spots increase the rate of excitation of Raman modes of the analyte molecules thereby enhancing the intensity of the Raman scattered light.

FIGS. 8-10 show simulation results of electric field formations around features for three different types of plasmonic electric field concentrators described above with reference to FIGS. 1-3, respectively, in accordance with embodiments of the present invention. The results were obtained using the well-known finite-difference time-domain method ("FDTD") described in *Computational Electrodynamics: The Finite-Difference Time-Domain Method*, Third Edition, by Allen Taflove and Susan C. Hagness, Artech House Publishers (Jun. 30, 2005).

Figure 8A:
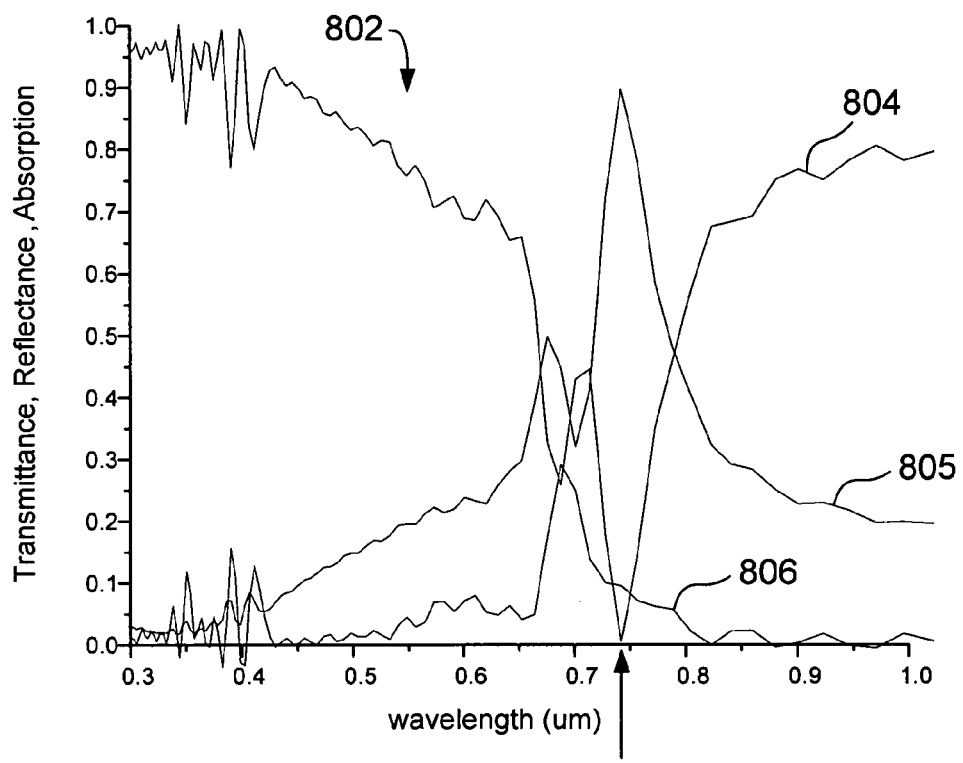
FIGS. 8-10 show simulation results of electric field formations around features for three different types of plasmonic electric field concentrators in accordance with embodiments of the present invention.
Figure 8B:
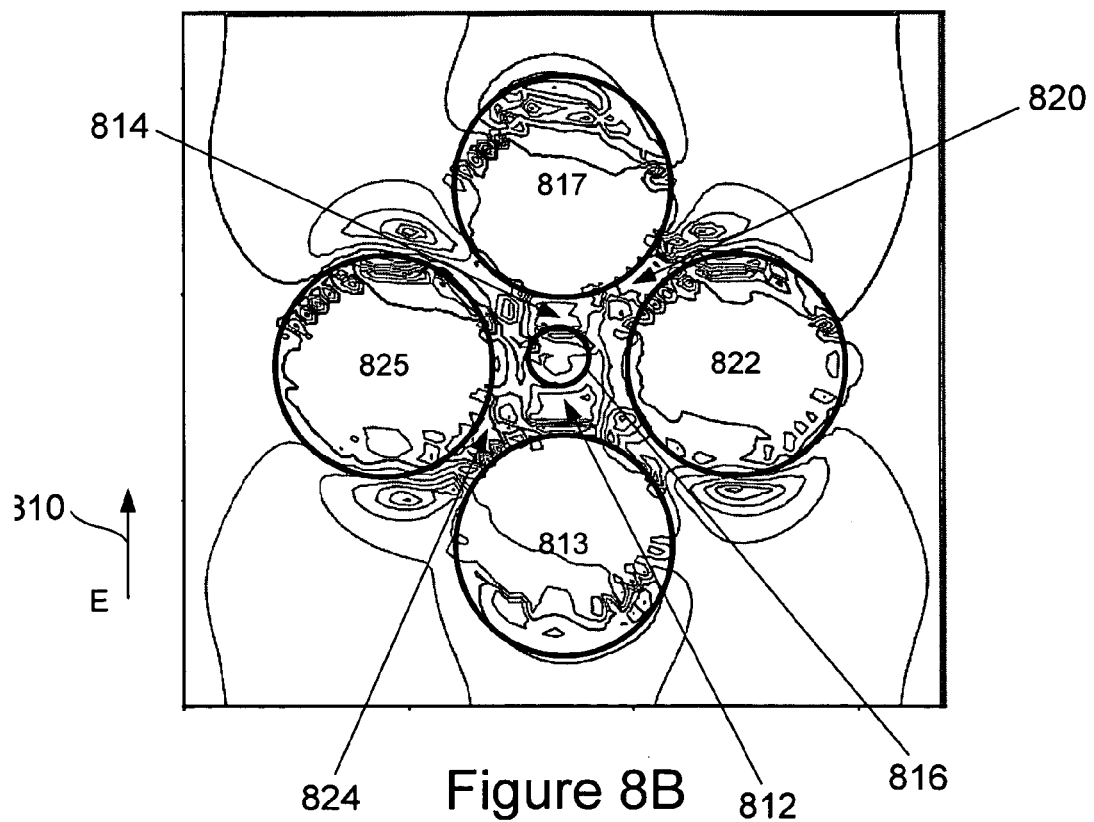

FIG. 8A shows a transmittance, reflectance, and absorption plot 802 for disk-shaped features of a PEFC with dimensions $r_1$ equal to 45 nm, $r_2$ equal to 15 nm, $d_1$ equal to 4.5 nm, and a thickness of 10 nm. Curves 804-806 corresponds to the transmittance, reflectance, and absorption of polarized light incident on the features over a range of wavelengths. Plot 802 reveals that at about 750 nm 804 the reflectance reaches about 0.9 and the transmittance drops to approximately zero. FIG. 8B shows a contour plot of the electric field intensities formed around the disk-shaped features of the PEFC. Polarized light is incident on the features with the direction of the electric field component identified by directional arrow 810. The contour plot reveals that the maximum electric field intensities or hot spots form in regions 812 and 814 between that small feature 816 and two large features 817 and 818. Other high intensity electric fields form in a region 820 between large features 817 and 822 and in a region 824 between large features 818 and 825.

Figure 9A:
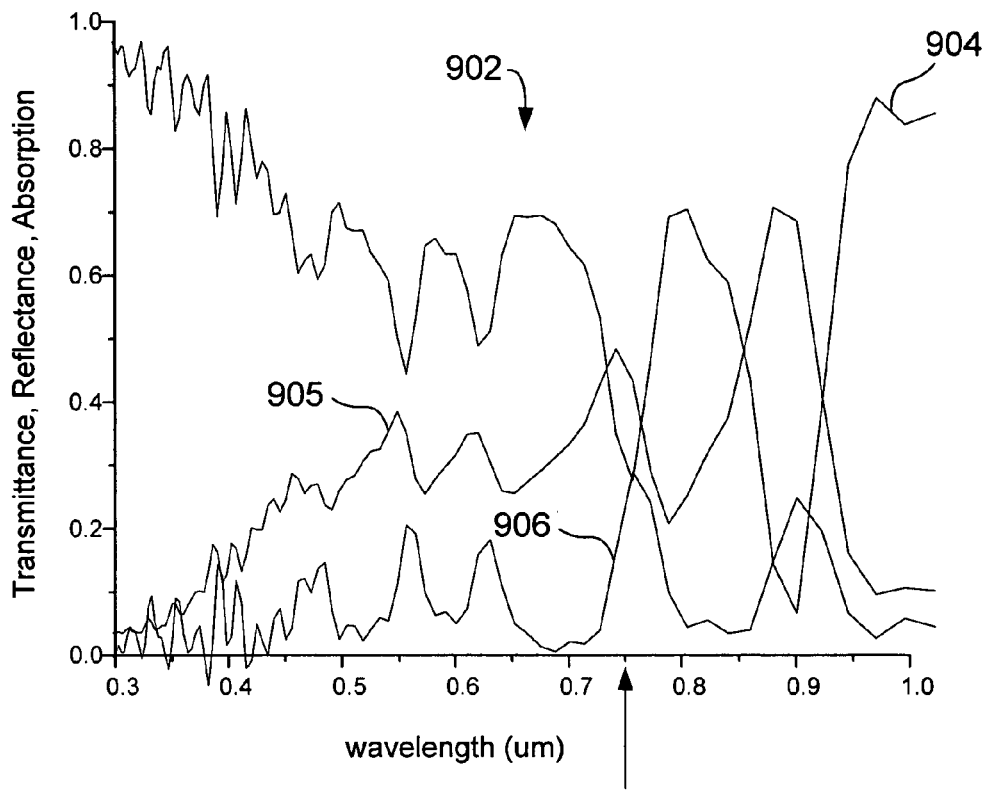
Figure 9B:
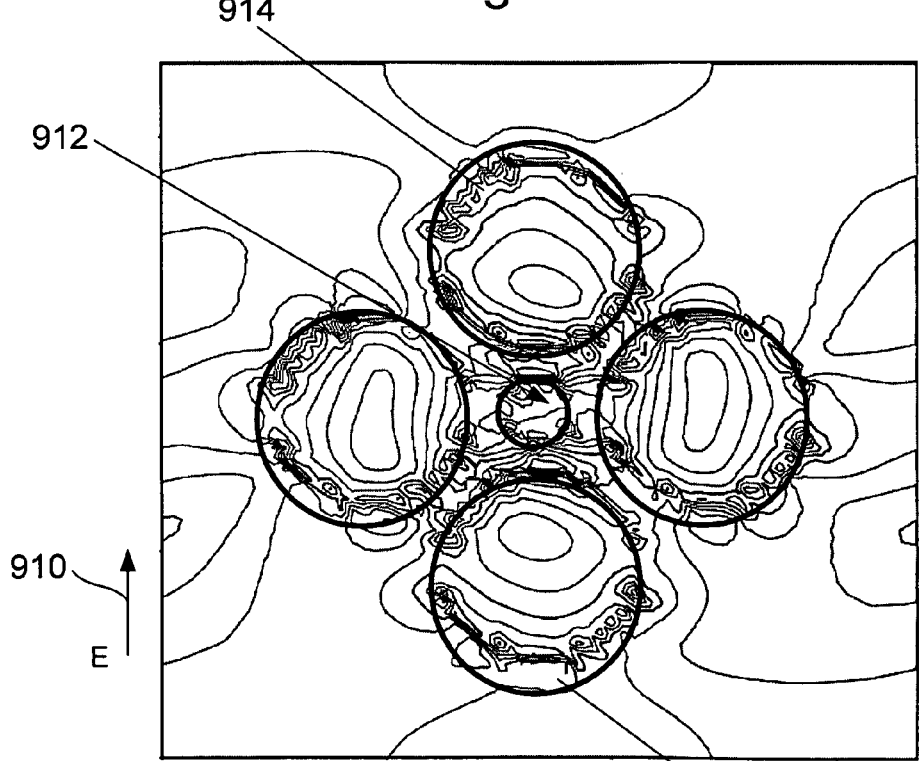

FIG. 9A shows a transmittance, reflectance, and absorption plot 902 for holes of a PEFC with dimensions $r_1$ equal to 45 nm, $r_2$ equal to 15 nm, $d_1$ equal to 4.5 nm, and a film thickness of 10 nm. Curves 904-906 corresponds to the transmittance, reflectance, and absorption of polarized light incident on the features over a range of wavelengths. FIG. 9B shows a contour plot of the electric field intensities around the holes of the PEFC. Polarized light is incident on the features with the direction of the electric field component identified by directional arrow 910. The contour plot reveals that the maximum electric field intensities or hot spots form within and near the edges of the central small hole, such as hot spot 912. FIG. 9B also reveals that high intensity electric fields form within the larger holes, such as regions 914 and 916

Figure 10A:
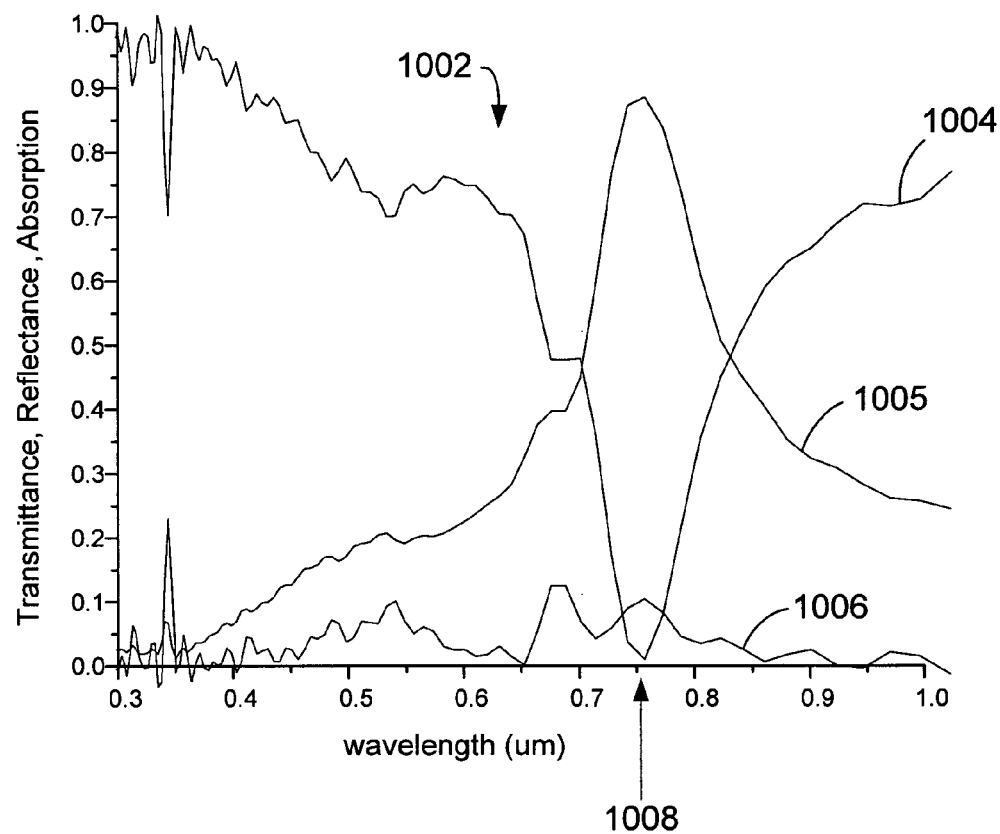
Figure 10B:
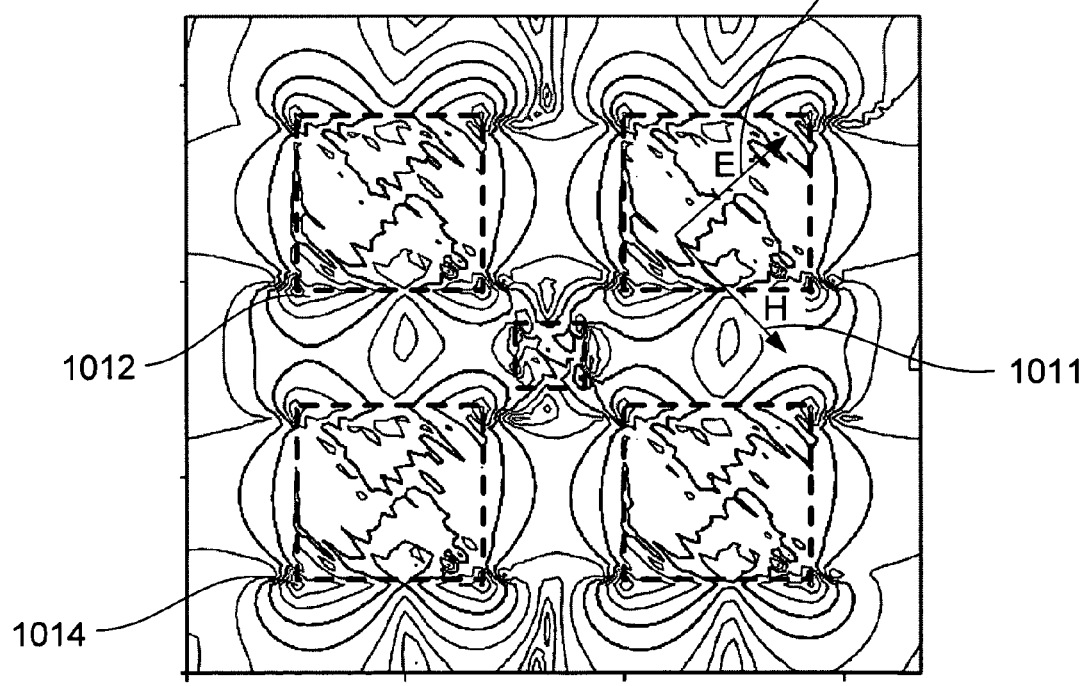

FIG. 10A shows a transmittance, reflectance, and absorption plot 1002 for cube-shaped features of a PEFC with dimensions $w_1$ equal to 90 nm, $w_2$ equal to 30 nm, $d_1$ equal to 4.5 nm. Curves 1004-1006 corresponds to the transmittance, reflectance, and absorption of polarized light incident on the features over a range of wavelengths. Plot 1002 reveals that at about 750 nm 1008 the reflectance reaches about 0.9 and the transmittance drops to approximately zero. FIG. 10B shows a contour plot of the electric field intensities around the cube-shaped features of the PEFC. Polarized light is incident on the features with the direction of the electric field component identified by directional arrow 1010 and magnetic field component 1011. For incident light with a wavelength of approximately 750 nm, the contour plot reveals that hot spots form around the corners of the larger features. For example, regions 1012 and 1014 represent two of 16 corners shown in FIG. 10B where hot spots form. Other high electric field intensity regions form around the edges of the cube-shaped features.

The amount of electromagnetic field enhancement can be quantified by determining the electromagnetic SERS enhancement factor $f^R$ at a coordinated position $r_m$ of a PEFC. The SERS enhancement factor $f^R$ can be estimated in terms of the local electric field $E_m$ at the position $r_m$ by:

$$f^R = (E_m/E_0)^4$$

where $E_0$ is the intensity of the electric field portion of the incident light. The SERS enhancement factor has been calculated for the disk-shaped features of the PEFC 200 and for the cuboid-shaped features of the PEFC 500 using FDTD. The electric field enhancement for light with a wavelength of 690 nm incident on the PEFC 800 comprising disk-shaped features with radial dimensions of $r_1$ equal to 45 nm, $r_2$ equal to 15 nm, separation distance $d_1$ equal to 4.5 nm, and feature thickness equal 10 nm produces $E_m/E_0$ of 120 and a SERS enhancement factor $f^R$ greater than $2 \times 10^8$. The electric field enhancement for light with a wavelength of 750 nm incident on the PEFC 900 comprising holes as features with radial dimensions also of $r_1$ equal to 45 nm, $r_2$ equal to 15 nm, separation distance $d_1$ equal to 4.5 nm, and feature thickness equal to 10 nm produces an $E_m/E_0$ of 115 and a SERS enhancement factor $f^R$ greater than $1.5 \times 10^8$. The electric field enhancement for light also with a wavelength of 750 nm incident on the PEFC 500 comprising cubic-shaped features with the edge lengths of the larger features equal to 90 nm, the edge lengths of the smaller feature equal to 30 nm, and a separation distance $d_2$ equal to 4.5 nm produces an $E_m/E_0$ of 47 and a SERS enhancement factor $f^R$ of approximately $5 \times 10^6$. Optimized geometry for cuboid structures produces f ☐ $4 \times 10^8$. The enhancement factors approach the values on the order of $\sim 10^{10}$ for structures with smaller gaps between smaller and larger features.

System for Performing Surface-Enhanced Raman Spectroscopy

Figure 11A:
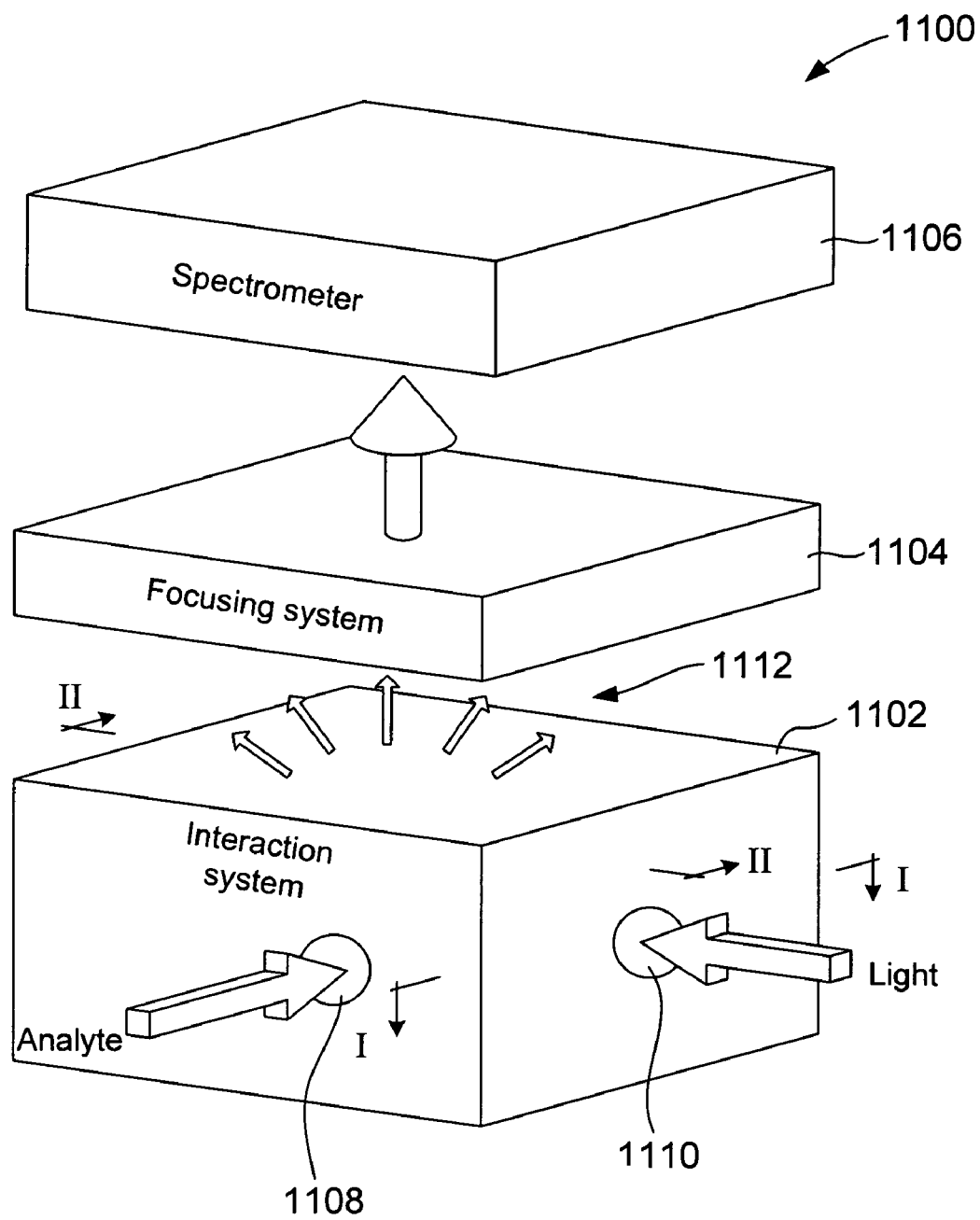
FIG. 11A shows an isometric view and schematic representation of a system for performing surface-enhanced Raman spectroscopy in accordance with embodiments of the present invention.

FIG. 11A shows an isometric view of a system 1100 for performing surface-enhanced Raman spectroscopy in accordance with embodiments of the present invention. The system 1100 comprises an interaction system 1102, a focusing system 1104, and a spectrometer 1106. As shown in FIG. 11, the interaction system 1102 includes an inlet channel 1108 through which an analyte enters the interaction system 1102 and a hollow waveguide 1110 through which incident light enters the interaction system 1102. The analyte can be in a liquid or gas phase. The interaction system 1102 can be composed of glass, acrylic, or another suitable transparent material. An interaction substrate (not shown) is disposed within the interaction system 1102 so that the analyte passes in close proximity to or is absorbed by features of the PEFCs of the interaction substrate and interacts with the incident light to produce enhanced Raman scattered light represented by directional arrows 1112. The focusing system 1104 collects and focuses at least a portion of the Raman scattered light onto a detector of the spectrometer 1106. The spectrometer 1106 generates a Raman spectrum that can then be interpreted to identify and/or characterize the analyte.

Figure 11B:
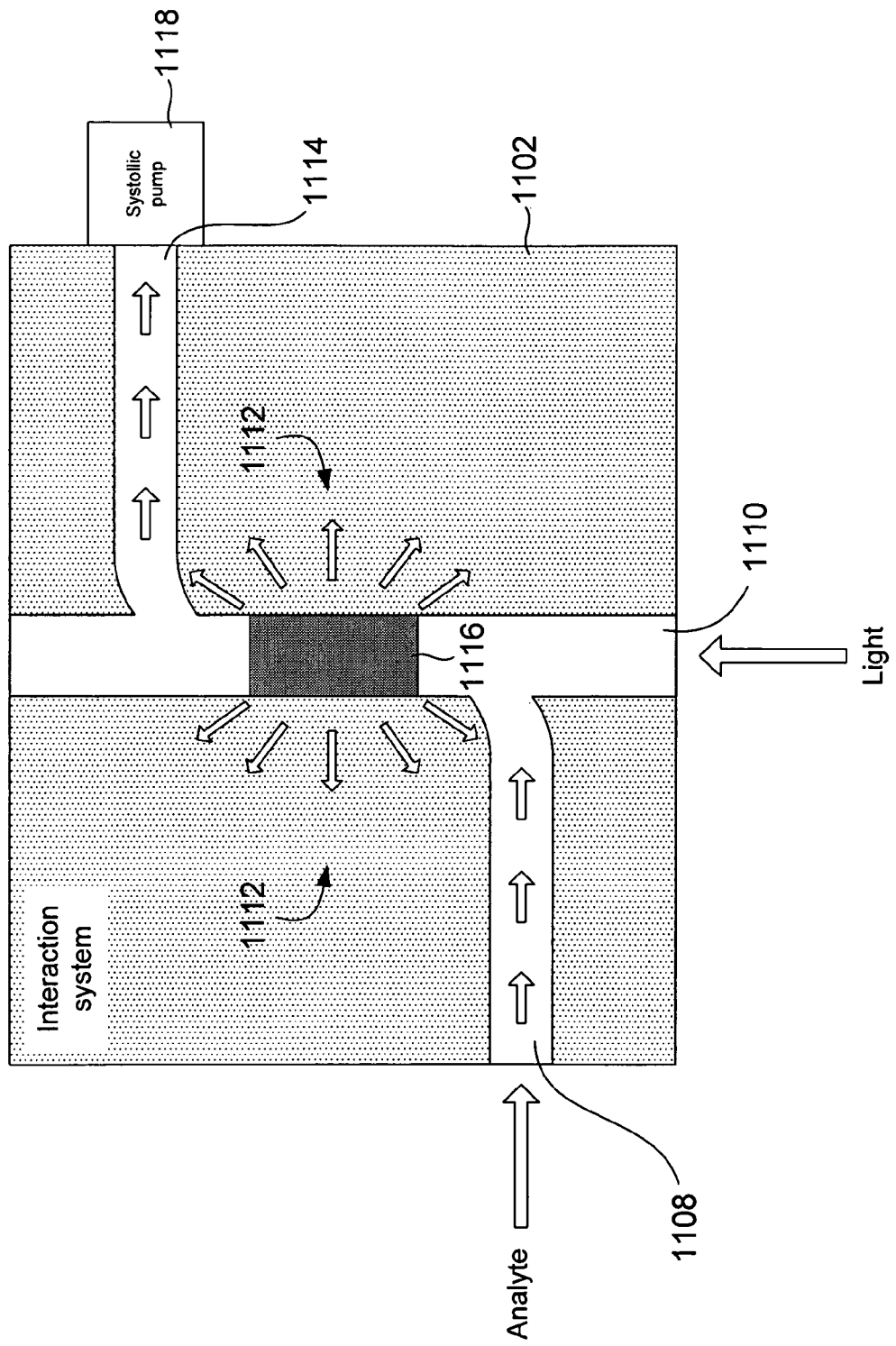
FIGS. 11B-11C show two different cross-sectional views of the interaction system along a lines I-I and II-II, respectively, shown in FIG. 11A, in accordance with embodiments of the present invention.
Figure 11C:
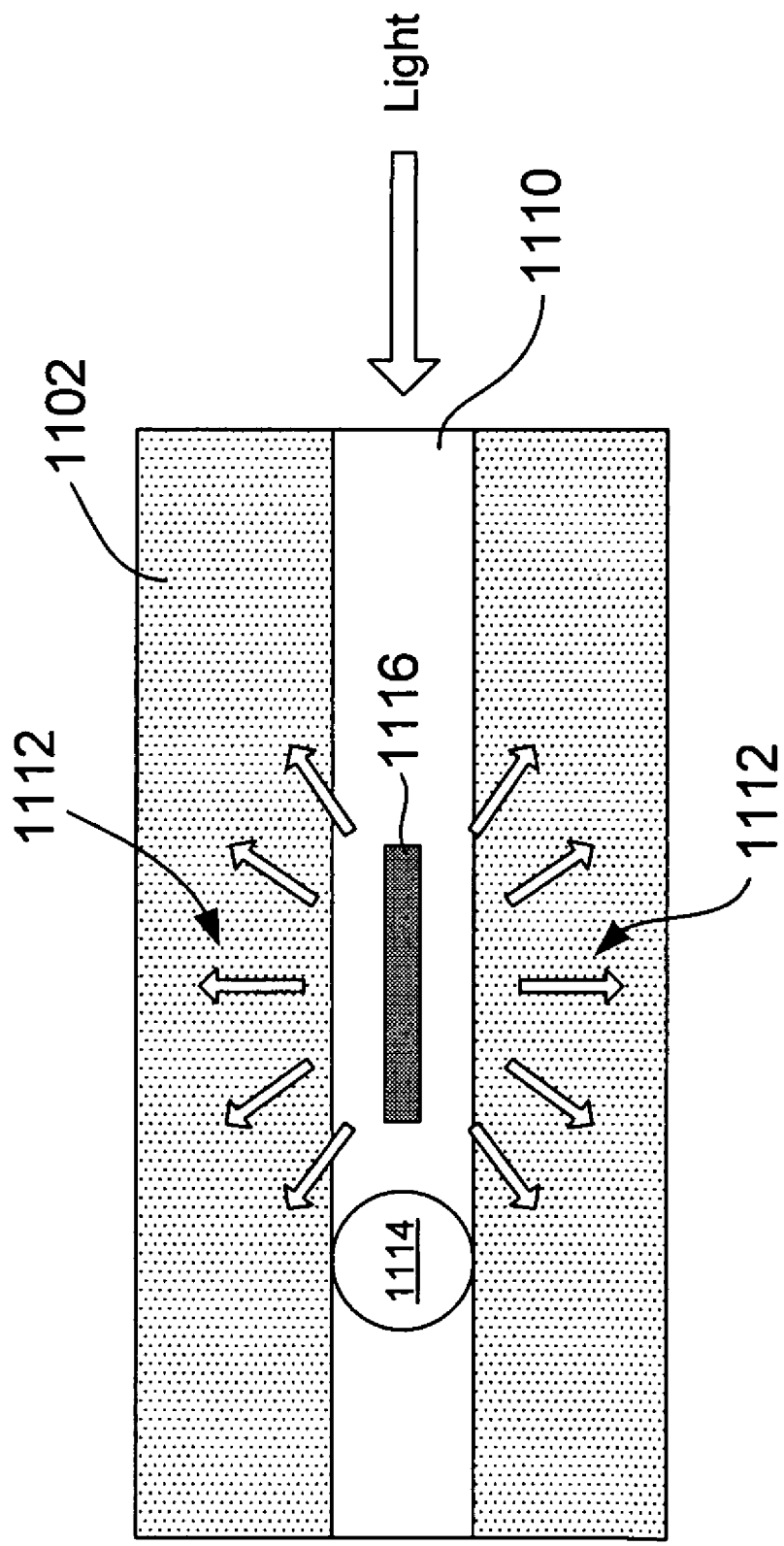

FIGS. 11B-11C show cross-sectional views of the interaction system 1102 along the lines I-I and II-II, respectively, shown in FIG. 11A, in accordance with embodiments of the present invention. FIG. 11B shows that the interaction system 1102 also includes an outlet channel 1114. The inlet channel 1108 and the outlet channel 1114 are hollow channels that branch from the hollow waveguide 1110. FIGS. 11B-11C also reveal an interaction substrate 1116 suspended within the hollow waveguide 1110 between the inlet channel 1108 and the outlet channel 1114 and configured as described above with reference to FIGS. 1-10. The analyte can be introduced to the inlet channel 1108. Capillary action, a systolic pump 1118, or other suitable device for moving an analyte in a gas or a liquid state can be used to draw the analyte into the hollow waveguide 1110 over the interaction substrate 1116 and out through the outlet channel 1114. While the analyte passes over the interaction substrate 1116, portions of the analyte can pass in close proximity to or be absorbed to features of the PEFCs of the interaction substrate 1116. Light striking the PEFCs enhances the electric field which in turn enhances the intensity of the Raman scattered light collected by the focusing system 1104. Note that in certain embodiments, portions of the hollow waveguide 1110 can include an optical grating on the sidewalls around the hollow waveguide 1110 in order to distribute the incident light more uniformly across the interaction substrate 1116.

Figure 12A:
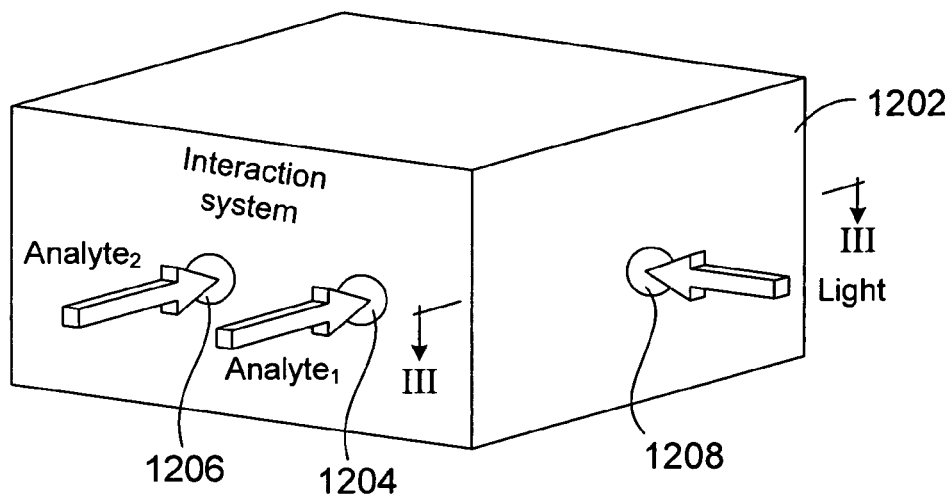
FIG. 12A shows an isometric view of an interaction system for receiving two different analytes in accordance with embodiments of the present invention.

In other embodiments, systems for performing surface enhanced Raman spectroscopy can be configured to receive two or more analytes and generate two or more corresponding Raman scatterings of light. FIG. 12A shows an isometric view of an interaction system 1202 for receiving two different analytes identified as Analyte$_1$ and Analyte$_2$ in accordance with embodiments of the present invention. The interaction system 1202 includes first and second inlet channels 1204 and 1206 through which the analytes Analyte$_1$ and Analyte$_2$ enter the interaction system 1202 and a hollow waveguide 1208 through which incident light enters the interaction system 1202. The analytes can both be in a liquid or a gas phase. The interaction system 1202 also includes two interaction substrates (not shown) disposed within the interaction system 1202 so that the first analyte Analyte$_1$ passes in close proximity to or is absorbed to features of the PEFCs of the first interaction substrate and the second analyte Analyte$_2$ passes in close proximity to or is absorbed to features of the PEFCs of the second interaction substrate. The interaction system 1202 can be composed of glass, acrylic, or another suitable transparent material.

Figure 12B:
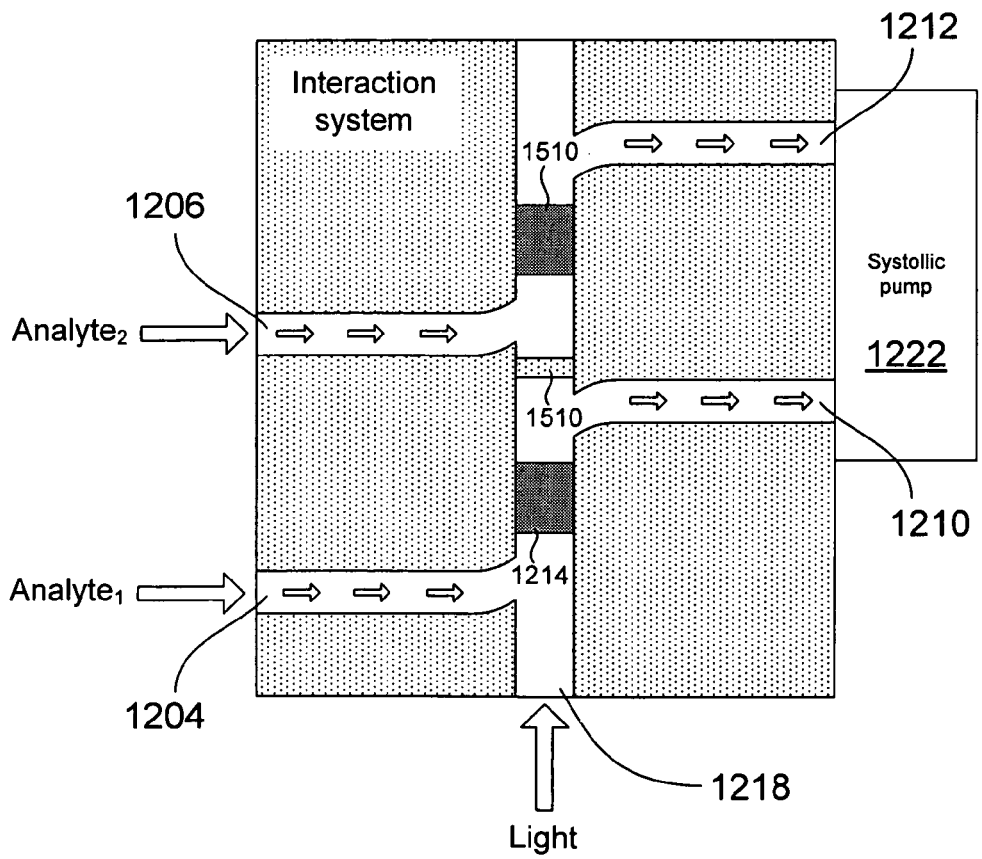
FIG. 12B shows a cross-sectional view of the interaction system along a line III-III, shown in FIG. 12A, in accordance with embodiments of the present invention.

FIG. 12B shows a cross-sectional view of the interaction system 1202 along a line III-III, shown in FIG. 12A, in accordance with embodiments of the present invention. FIG. 12B shows that the interaction system 1202 also includes first and second outlet channels 1210 and 1212. The inlet channels 1204 and 1206 and the outlet channels 1210 and 1211 are hollow channels that branch from the hollow waveguide 1208. First and second interaction substrates 1214 and 1216 are configured as described above with reference to FIGS. 1-10 and disposed within the hollow waveguide 1208. The analytes Analyte$_1$ and Analyte$_2$ enter the inlets channel 1204 and 1206, respectively. The interaction system 1202 can include a transparent barrier 1220 that prevents the analytes from combining. Capillary action, a systolic pump 1222, or other suitable device for moving an analyte in a gas or a liquid state can be used to draw the analytes into the hollow waveguide 1208 so that Analyte$_1$ passes over the interaction substrate 1214 and out through the first outlet channel 1210 and Analyte$_2$ passes over the interaction substrate 1214 and out through the second outlet channel 1212. While the analytes pass over the interaction substrates 1214 and 1216, light striking the PEFCs of the interaction substrates 1214 and 1216 enhances the electric field which in turn enhances the intensity of the Raman scattered light emanating from the analytes. Portions of the hollow waveguide 1208 can include an optical grating on the sidewalls around the interactions substrates 1214 and 1216 in order to distribute the incident light more uniformly across the interaction substrates 1214 and 1216.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A plasmonic electric-field concentrator comprising:
two or more features having a first size; and
a feature having a second size that is similar in shape and positioned adjacent to the two or more features, wherein the second size is relatively smaller than the first size, and the features are arranged so that when light of an appropriate wavelength is incident on the features, surface plasmon polaritons form on the outer surfaces of the features such that the electric field produced by the smaller feature combines with the electric fields produced by adjacent larger features to amplify the intensity of the electric field around the features to create electric field hot spots.

2. The concentrator of claim 1 wherein the features further comprise metallic plates.

3. The concentrator of claim 1 wherein the features further comprise holes in a thin metallic film.

4. The concentrator of claim 1 wherein the features further comprise disk-shaped, square, rectangular, or elliptical geometries.

5. The concentrator of claim 1 wherein the features further comprise metallic polyhedral objects.

6. The concentrator of claim 1 wherein the features further comprise one of: gold, silver, and copper.

7. The concentrator of claim 1 further comprising a substrate upon which the features are disposed.

8. The concentrator of claim 7 wherein the substrate further comprises one of: glass, $SiO_2$, quartz, silicon nitride, polymer or another suitable dielectric material.

9. The concentrator of claim 7 wherein the substrate further comprises recesses to retain polyhedron-shaped features.

10. An interaction substrate comprising an array of one or more plasmonic electric-field concentrators configured in accordance with claim 1.

11. A system for performing Raman spectroscopy comprising:
- an interaction system having an inlet channel and an outlet channel that branch from a hollow waveguide, and an interaction substrate disposed within the hollow waveguide between the inlet channel and the outlet channel;
- a focusing system to collect and focus a portion of Raman scattered light to be emitted from an analyte and to pass through the interaction system, when the analyte interacts with the interaction substrate and light guided to the interaction substrate via the hollow waveguide; and
- a spectrometer to receive the focused Raman scattered light for analysis.

12. The system of claim 11 further comprising a systolic pump to move an analyte in a gas or a liquid state through the inlet channel over the interaction substrate and out of the interaction system through the outlet channel.

13. The system of claim 11 wherein the interaction system further comprises one of: glass, acrylic, quartz, and a transparent polymer/plastic.

14. The system of claim 11 wherein the interaction substrate further comprises an array of one or more plasmonic electric-field concentrators.

15. The system of claim 14 wherein the plasmonic electric-field concentrators further comprises:
- two or more features having a first size; and
- a feature having a second size that is similar in shape and positioned adjacent to the two or more features, wherein the second size is relatively smaller than the first size, and the features are arranged so that when the light is incident on the features, surface plasmon polaritons form on the outer surfaces of the features such that the electric field produced by the smaller feature combines with the electric fields produced by adjacent larger features to amplify the intensity of the electric field around the features to create electric field hot spots.

16. The system of claim 15 wherein the features further comprise metallic plates.

17. The system of claim 15 wherein the features further comprise holes in a thin metallic film.

18. The system of claim 15 wherein the features further comprise disk-shaped, square, rectangular, or elliptical geometries.

19. The system of claim 15 wherein the features further comprise metallic polyhedral objects.

20. The system of claim 15 further comprising a substrate upon which the features are disposed.

* * * * *

UNITED STATES PATENT AND TRADEMARK OFFICE
CERTIFICATE OF CORRECTION

| | | |
|---|---|---|
| PATENT NO. | : 7,995,201 B2 | Page 1 of 1 |
| APPLICATION NO. | : 12/287549 | |
| DATED | : August 9, 2011 | |
| INVENTOR(S) | : Alexandre M. Bratkovski et al. | |

It is certified that error appears in the above-identified patent and that said Letters Patent is hereby corrected as shown below:

In column 7, lines 27-28, delete "the hots the hot" and insert -- the hot --, therefor.

Signed and Sealed this
Tenth Day of April, 2012

David J. Kappos
*Director of the United States Patent and Trademark Office*